(12) United States Patent
Zbinden

(10) Patent No.: US 11,175,273 B1
(45) Date of Patent: Nov. 16, 2021

(54) EARTH SOIL ELECTRODE INSTALLATION AND REMOVAL DEVICE

(71) Applicant: Adam Zbinden, Walnut Creek, CA (US)

(72) Inventor: Adam Zbinden, Walnut Creek, CA (US)

(*) Notice: Subject to any disclaimer, the term of this patent is extended or adjusted under 35 U.S.C. 154(b) by 0 days.

(21) Appl. No.: 16/941,491

(22) Filed: Jul. 28, 2020

(51) Int. Cl.
*G01N 33/24* (2006.01)
*G01N 1/08* (2006.01)
*G01N 27/30* (2006.01)
*E21B 11/00* (2006.01)

(52) U.S. Cl.
CPC ............ *G01N 33/24* (2013.01); *E21B 11/005* (2013.01); *G01N 1/08* (2013.01); *G01N 27/30* (2013.01)

(58) Field of Classification Search
CPC .......... G01N 1/08; G01N 27/30; G01N 33/24; G01N 33/246; G01N 2033/243; G01N 2033/245; E21B 3/00; E21B 11/005
See application file for complete search history.

(56) References Cited

U.S. PATENT DOCUMENTS

| | | | | |
|---|---|---|---|---|
| 3,316,983 A | * | 5/1967 | Goodman | E21B 11/005 173/216 |
| 3,896,890 A | * | 7/1975 | Gale | E02D 5/801 175/19 |
| 4,387,483 A | * | 6/1983 | Larrabee | E02D 5/801 16/422 |
| 2017/0254766 A1 | * | 9/2017 | Bermudez Rodriguez | G01N 27/048 |

* cited by examiner

*Primary Examiner* — Benjamin R Schmitt

(57) ABSTRACT

A device for the manual installation and removal of conductive sensor electrodes into and from the earth for repeated testing of soil electrical properties, utilizing a screw machine principle to drive electrodes fabricated with an auger or drill structure and with a hardware fitting at the electrode top. A user can stabilize the device with their mass while standing on the ground interface platforms, which are connected to the device with angled rigid support members, and then actuate the electrode driving mechanism with ergonomic grips attached perpendicularly to a dual moment arm lever. The device can also rotate along a single axis to drive electrodes at specific angles.

1 Claim, 5 Drawing Sheets

EARTH SOIL ELECTRODE INSTALLATION AND REMOVAL DEVICE

BACKGROUND OF THE INVENTION

To determine the electrical properties of earthen soil, it is often required to install conductive electrodes into the earth. For performing many repeated electrical tests on the soil, wherein the installation and removal of electrodes from the earth is a frequent and ongoing task, a tool which minimizes operator labor and optimizes the installation and removal of the electrode is desirable.

SUMMARY OF THE INVENTION

The present invention teaches an earth soil installation & removal tool for electrodes which are fabricated with an auger or drill shape, and which have hardware fittings at the head. The present invention features a manually operated electrode drive column and uses a screw machine principle to direct a kinetic force onto the electrode top with a vector path which is directed into the earth soil. It has support members which, when extended to the ground, feature attached oversized platforms on which the user stands when actuating the handles to turn the dual lever moment arm, which is the prime mover for the electrode driving mechanism. An electrode with a hex-head hardware pattern at its top can be inserted into a magnetic receptacle at the base of the electrode driving column of the device, and then torqued into the soil, with the electrode drive column stabilized by the normal static force resulting from the operator's mass applied at the base of the device while standing with one foot on each ground interface platform. When the electrode has been driven to an appropriate depth, the machine can be lifted off the electrode head. For removal, the electrode head and the receptacle on the electrode drive column's base can be re-attached and the direction of torque application reversed. The device features two ground platforms for the operator to stand on while actuating the moment arm lever.

DETAILED DESCRIPTION OF THE INVENTION

Figure 1:
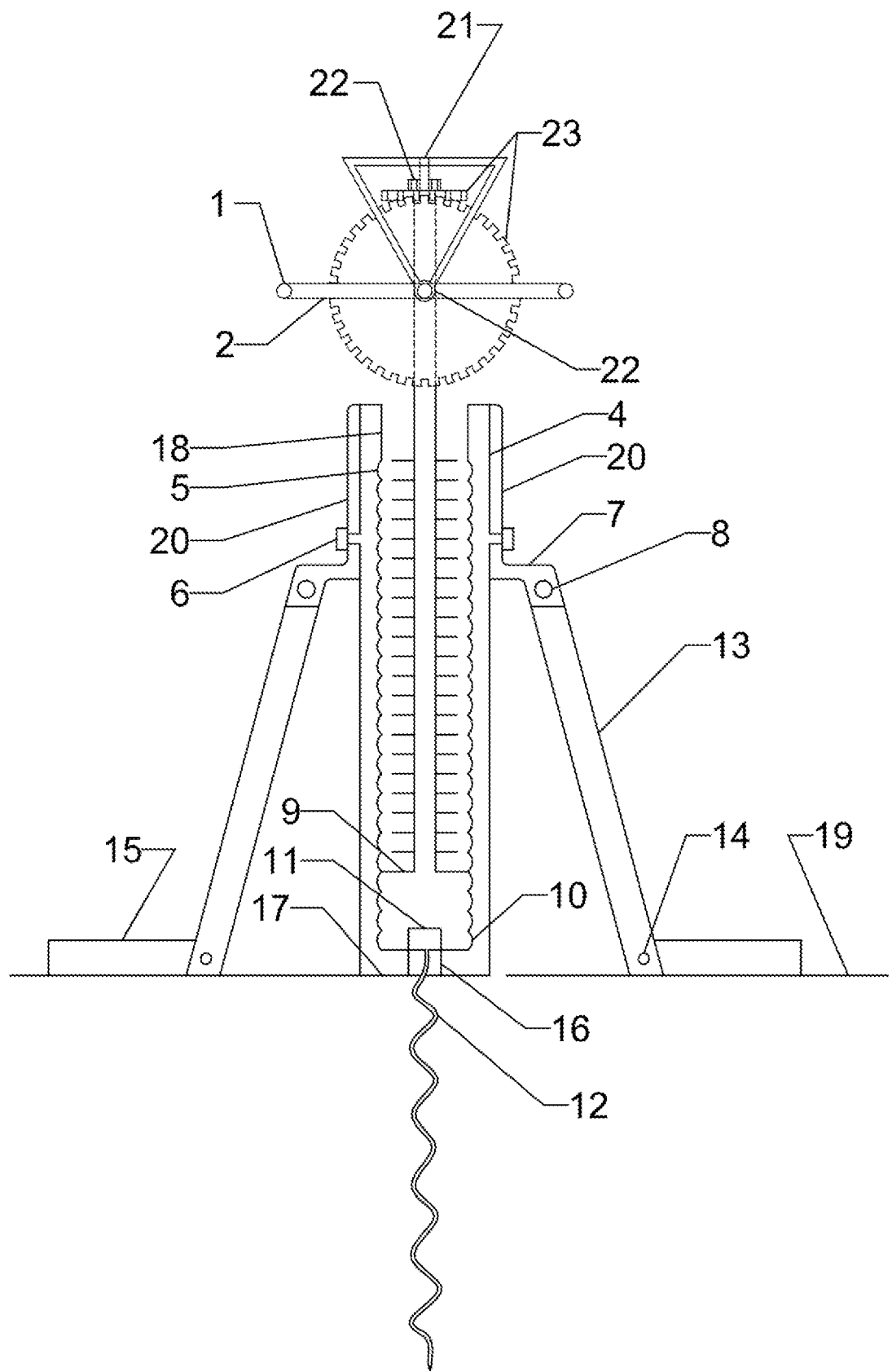
FIG. 1 is a profile view of the present invention, which shows the total internal componentry of the electrode driving system, when an electrode has been driven into the soil by the device.
Figure 2:
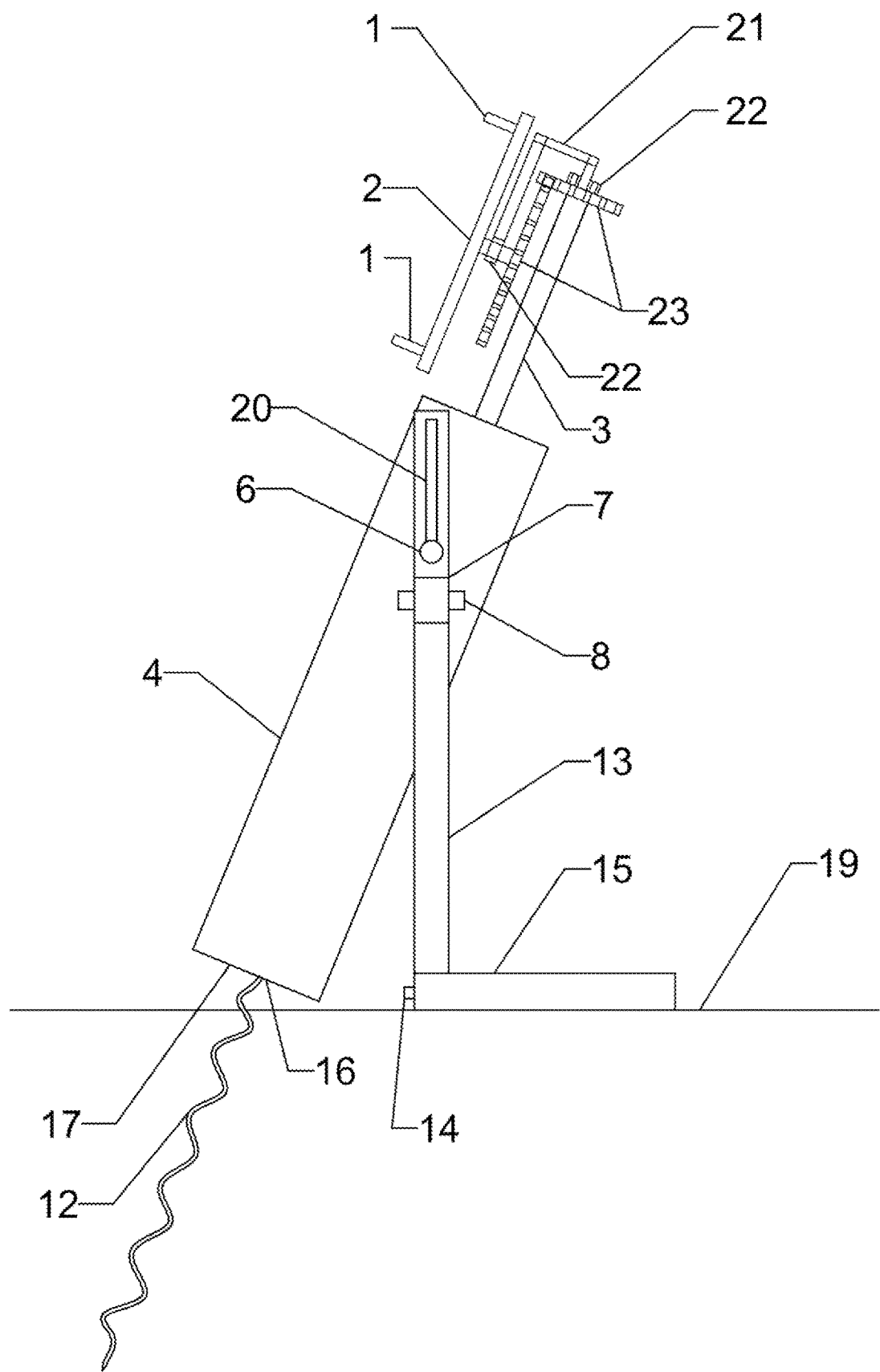
FIG. 2 is an adjacent profile view of the present invention, wherein the potential for perpendicular axial plane rotation of the support members relative to the electrode drive column is demonstrated, such that the electrode drive column is driving an electrode at an angle, while the base comprised of the support members and platforms remains level relative to the soil grade.
Figure 3:
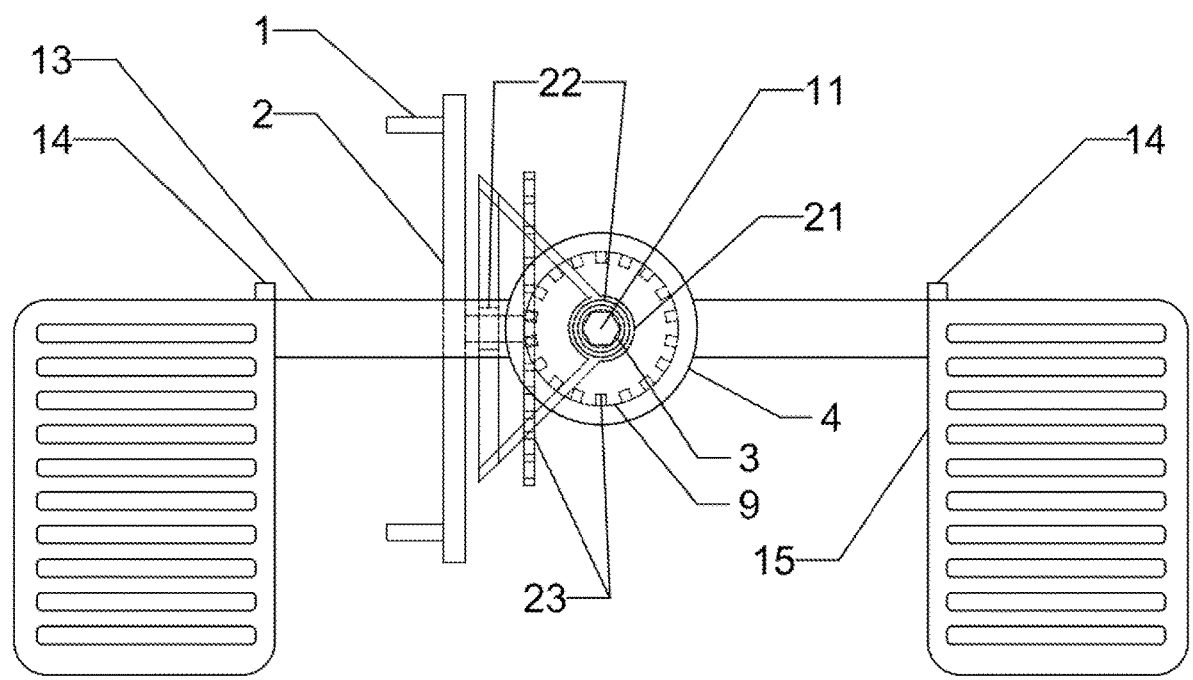
FIG. 3 is a section view of the present invention, as seen from the base of the electrode drive column, where the electrode hardware interfaces with the receptacle on the electrode grip of the drive mechanism.
Figure 4:
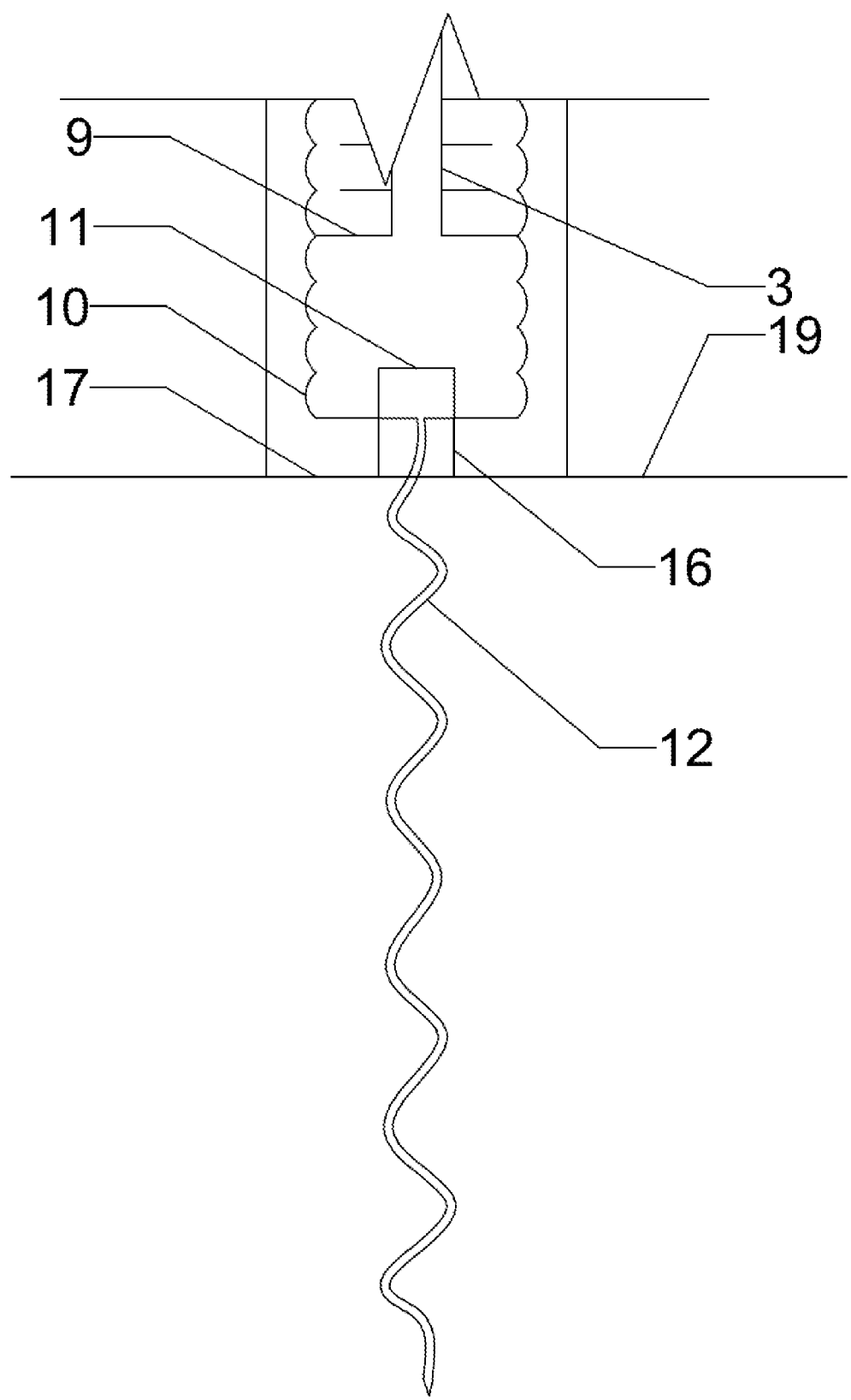
FIG. 4 is a detailed view of the electrode driving mechanism's interface with the soil top-grade when installing an electrode into the ground.
Figure 5:
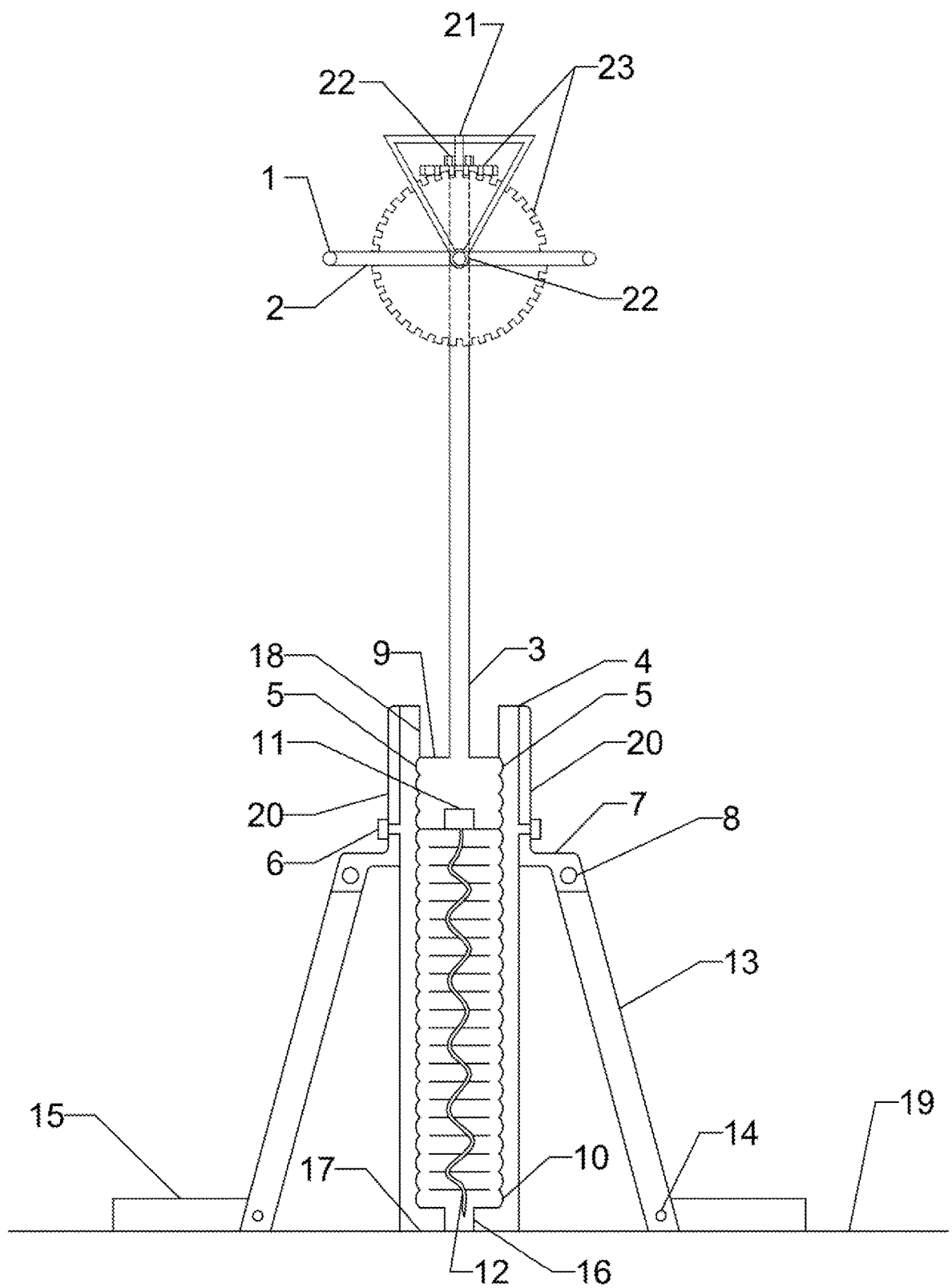
FIG. 5 shows the electrode fully retracted inside of the cylindrical chamber and drill casing, such as when the electrode is about to be installed into the ground, or after its subsequent removal.

1 is a pair of ergonomically cushioned grips which are integrated with the center-pivoting dual moment arm lever 2, which is coupled with the electrode-driving axle 3 via a pair of speed reducing and torque increasing gears 23, orthogonally oriented, and connected through slip ring bearings 22 integrated with a triangular mounting bracket 21 which allows for free spinning rotation of the grips 1, dual moment arm lever 2, gears 23, and electrode driving axle 3, while the triangular mounting bracket 21 mechanically integrates 1, 2, 23, and 3 and enables the free rotation of these components with the integrated slip ring bearing mechanisms 22. Coupled to the opposite end of 3 is the electrode-driving grip 9, with a hardware head receptacle 11 which matches the geometry of the metallic electrode 12 at the topmost point of 12. Housing and containing the electrode-driving arm 3 and electrode driving grip 9 is a durable outer casing 4 which contains an internally threaded section, with upper extent shown with 5 and the lower extent shown with 10, with the length of this internally threaded section defining the amount of electrode-driving distance potential. 1, 2, and all components contained within 4 are axially aligned to be colinear, and are supported on a column structure by the dual support members 13, which attach to 4 with a bracket 7 which allows the support members 13 to fold and extend on an adjustable hardware axis shown with 8, and the vertical column comprised of 1, 2, and the components housed within 4 can rotate on a perpendicular plane, using a hardware axis shown with 6, relative to the support members 13. The electrode driving column support members 13 are stabilized at the ground interface contact point with large surface area platforms 15, which can pivot vertically about a hardware axis shown with 14. The base of the electrode drive column is depicted with 17 and forms an interface with the soil top-grade 19, and 17 is materially integrated with the casing material 4, while in the center of 17 is a channel inlet & outlet 16 for the electrode 12, where the electrode channel 16 is a hollow tube bored through the base of the casing material 4, and 16 terminates at the bottom extent 10 of the threaded region of the cylinder chamber 18 which is internal to the casing 4, where 18 contains the screw drive machine comprising the electrode driving axle 3 and electrode grip 9 with recess 11, which combined move linearly within 18 between 5 and 10 as 3 transfers the torque applied by the angular rotation of 1 & 2 during operation, and the drive mechanism comprised of 3,9,11 is removable at the top of 18 and 4, or at the top of the device, for lubrication and maintenance. While the bracket 7 interfaces the drill body comprised of the cylinder chamber 18 and the casing 4 with the support members 13, a hollow guiderail 20 is integrated with the vertical segment of 7 which is flush with 4, to allow the vertical raising of the drill body comprised of 18 and 4 relative to the soil-top-grade, by adjusting the bolt tension of the hardware axis 6 which is rigidly and permanently attached to the cylinder chamber 18 through the casing 4 to support the drill body in a vertically elevated position.

To install an electrode into the ground using the device, first rotate the electrode grip to the top of the threaded segment of the internal sleeve, and insert the head of the electrode through the channel in the casing at the base and into the magnetic receptacle of the grip. Level the device on the ground at the location intended for electrode installation, stand with one foot on each of the platform, effectively standing over and straddling the device. Apply torque to the handles until the desired depth has been reached. Then lift the device off the buried electrode.

The topmost location of the electrode driving axle 3 is solidly and rigidly coupled to the horizontally oriented gear, such that a rotation of the horizontal gear directly results in a corresponding rotation of the electrode driving axle, while a circular bearing exists in the hollow center of the horizontal gear, which connects with a rigid shaft end of the support bracket, such that the support bracket is anchored to this topmost location while being de-coupled from rotation. The other end of the support bracket is comprised of a hollow ring, with a circular bearing in its center, which interfaces with the shaft which connects the vertically aligned gear to the dual moment arm lever and grips, which are also solidly and rigidly coupled, such that a rotation of the dual moment arm lever via the grips results in a direct and corresponding rotation of the vertically aligned gear, and the vertically aligned gear has teeth which are mechanically linked to the teeth of the horizontally aligned gear to form a coupled speed-torque conversion system. The support bracket has two ends. One end has a ring structure with an integrated circular bearing, and this bearing center is coupled with a shaft which links the dual moment arm lever to the vertically aligned gear, such that the moment arm lever, linking shaft, and vertical gear can rotate freely while the connected end of the support bracket is stationary and decoupled from this rotation. The other or second end of the support bracket is a cylindrical shaft, vertically oriented orthogonal to the center point of the horizontal gear, and coupled with the inside of a circular bearing which is integrated with the center of the horizontal gear, such that the rotation of the horizontal gear and its solidly coupled electrode driving axle is decoupled from the connected support shaft of the support bracket end, such that the support bracket has an anchoring point comprised of said support axle for statically supporting the mass of the dual moment arm lever and the vertical gear at the location of the shaft which links these two components. The top end of the support bracket, which is connected to the inner region of a circular bearing integrated with the horizontal gear, statically supports the vertical gear and the dual moment arm lever, and maintains the coupling of the horizontal and vertical gears, by retaining the interlinking shaft which connects the vertical gear and dual moment arm lever within a ring-structure at this support bracket end which has a circular bearing within which the dual moment arm, vertical gear, and their interlinking shaft can freely spin, with rotation decoupled from the stationary support bracket. The support bracket has a solid shaft at its top location, which connects with the center of the horizontal gear, and the support bracket has a ring with integrated circular bearing at its bottom location, which encircles and supports the dual moment arm lever and vertical gear via their interlinking connection shaft. The support bracket remains stationary while the moment arm lever, mechanically coupled vertical and horizontal gears, and electrode driving shaft rotate, and maintains the coupling of the teeth of the vertical and horizontal speed reducing, torque increasing gears by anchoring to the center location of the horizontal gear at the top location of the bracket and holding and supporting the vertical gear and dual moment arm lever about their linking shaft within a circular bearing integrated within a ring structure located at the bottom location of the bracket.

The invention claimed is:

1. A device for manually advancing a metallic electrode into an earth location to establish a ground electrical potential, which features subsequent electrode retraction capabilities, comprising:
   an electrode driving column, comprising:
   a cylindrical chamber, with an internally threaded segment extending from a base region of said chamber to a top region of said chamber, wherein a length of the internally threaded segment defines a drive length potential for an electrode;
   an outer casing which houses the internally threaded cylindrical chamber, wherein said outer casing extends beyond the base and top regions of said cylindrical chamber;
   an electrode driving axle coupled to a threaded electrode grip which rotates within the internally threaded segment of the cylindrical chamber as a screw machine, wherein the electrode grip integrates a hardware head receptable with a magnetic base which attaches to a head of an electrode;
   a pair of handles which connect to a dual moment arm lever, wherein said dual moment arm lever couples at a center location with a perpendicular axle, wherein said axle is connected to a center axial rotation point of a first gear, and said first gear is coupled with a second orthogonally oriented gear, wherein said second gear connects at a center axial rotation point to the electrode driving axle at a topmost location of said electrode driving axle, and a gearset comprised of said first and second gears is supported by a mounting bracket which attaches to the first and second gears at their center axial rotation points with a pair of rotating slip ring circular bearings;
   a pair of rigid support members, wherein each support member connects to the electrode driving column at a location on the outer casing, and
   a pair of earth contact load bearing platforms, wherein each platform connects respectively to an end of the corresponding support member which is opposite from an end which is connected to the outer casing.

* * * * *